United States Patent
Scanlan et al.

(10) Patent No.: US 9,672,662 B2
(45) Date of Patent: Jun. 6, 2017

(54) METHOD FOR CREATING A SURGICAL RESECTION PLAN FOR TREATING A PATHOLOGICAL DEFORMITY OF A BONE

(71) Applicants: Smith & Nephew, Inc., Memphis, TN (US); A2 SURGICAL, Lemans (FR)

(72) Inventors: Sean Scanlan, Winchester, MA (US); Stephane LaVallee, St Martin D'Auriage (FR); Laurence Chabanas, Saint-Pierre-d'Allevard (FR); Asheesh Bedi, Ann Arbor, MI (US); Thomas Byrd, Nashville, TN (US); Bryan Kelly, Riverside, CT (US); Christopher Larson, Edina, MN (US)

(73) Assignees: Smith & Nephew, Inc., Memphis, TN (US); A2 Surgical, LeMans (FR)

( * ) Notice: Subject to any disclaimer, the term of this patent is extended or adjusted under 35 U.S.C. 154(b) by 0 days.

(21) Appl. No.: 14/906,679

(22) PCT Filed: Jul. 25, 2014

(86) PCT No.: PCT/EP2014/066014
§ 371 (c)(1),
(2) Date: Jan. 21, 2016

(87) PCT Pub. No.: WO2015/011256
PCT Pub. Date: Jan. 29, 2015

(65) Prior Publication Data
US 2016/0253846 A1 Sep. 1, 2016

(30) Foreign Application Priority Data
Jul. 25, 2013 (EP) ..................... 13306077

(51) Int. Cl.
*G06T 19/20* (2011.01)
*G06T 7/00* (2017.01)
(Continued)

(52) U.S. Cl.
CPC .............. *G06T 19/20* (2013.01); *A61B 5/055* (2013.01); *A61B 5/4504* (2013.01); *A61B 5/4571* (2013.01); *A61B 6/032* (2013.01); *A61B 6/505* (2013.01); *A61B 8/0875* (2013.01); *A61B 8/483* (2013.01); *A61B 34/10* (2016.02); *G06F 3/04815* (2013.01); *G06F 3/04845* (2013.01);
(Continued)

(58) Field of Classification Search
None
See application file for complete search history.

(56) References Cited

U.S. PATENT DOCUMENTS 5,086,401 A * 2/1992 Glassman .............. A61B 34/20
606/53
7,949,386 B2 * 5/2011 Buly .................... A61B 5/1121
345/629

(Continued)

OTHER PUBLICATIONS

Charbonnier et al., "An Integrated Platform for Hip Joint Osteoarthritis Analysis", International Journal of Computer Assisted Radiology and Surgery Manuscript No., pp. 1-8.
(Continued)

*Primary Examiner* — Ashish K Thomas

(57) ABSTRACT

The invention relates to a method for creating a surgical resection plan for treating a pathological deformity of a bone.

19 Claims, 6 Drawing Sheets

(51) Int. Cl.
*A61B 34/10* (2016.01)
*A61B 5/055* (2006.01)
*A61B 5/00* (2006.01)
*A61B 6/03* (2006.01)
*A61B 6/00* (2006.01)
*A61B 8/08* (2006.01)
*G06F 3/0481* (2013.01)
*G06F 3/0484* (2013.01)
*G06T 17/00* (2006.01)

(52) U.S. Cl.
CPC .......... *G06T 7/0014* (2013.01); *G06T 7/0022* (2013.01); *G06T 7/0044* (2013.01); *G06T 7/0051* (2013.01); *G06T 7/0081* (2013.01); *G06T 7/0091* (2013.01); *G06T 17/00* (2013.01); *A61B 2034/105* (2016.02); *G06T 2207/10072* (2013.01); *G06T 2207/10081* (2013.01); *G06T 2207/10088* (2013.01); *G06T 2207/10136* (2013.01); *G06T 2207/30008* (2013.01)

(56) References Cited

U.S. PATENT DOCUMENTS

| | | | | |
|---|---|---|---|---|
| 8,639,020 | B1* | 1/2014 | Kutliroff | G06T 7/0071 345/420 |
| 8,786,680 | B2* | 7/2014 | Shiratori | G06F 3/011 345/156 |
| 2005/0148843 | A1* | 7/2005 | Roose | A61B 17/17 600/407 |
| 2008/0074427 | A1* | 3/2008 | Barth | A61B 17/88 345/502 |
| 2009/0163922 | A1* | 6/2009 | Meridew | A61F 2/4609 606/88 |
| 2011/0093086 | A1* | 4/2011 | Witt | A61F 2/3609 623/22.15 |
| 2011/0301654 | A1* | 12/2011 | Wozencroft | A61B 17/1668 606/86 R |
| 2013/0114866 | A1 | 5/2013 | Kasodekar et al. | |
| 2014/0165365 | A1* | 6/2014 | Fargahi | A61F 2/95 29/515 |

OTHER PUBLICATIONS

Nishii et al., "Three-Dimensional Cartilage Thickness Distribution of Dysplastic Hips with and without Osteoarthritis: Assessment with a Fully Automated Computer Analysis from 3D MR Imaging", Proc. Intl. Soc. MAG. Reson. Med. 11, 2003, p. 1518.

Cobb et al., "Cams and Pincer Impingement are Distinct, Not Mixed: The Acetabular Pathomorphology of Femoroacetabular Impingement", Clin Orthop Relat Res, vol. 468, No. 8, 2010, pp. 2143-2151.

Kohnlein et al., "Acetabular Morphology: Implications for Joint-Preserving Surgery", Clin Orthop Relat Res, vol. 467, No. 3, 2009, pp. 682-691.

Murphy et al., "Acetabular Dysplasia in the Adolescent and Young Adult", No. 261, Dec. 1990, pp. 214-223

International Search Report from corresponding application No. PCT/EP2014/066014, dated Oct. 31, 2014.

* cited by examiner

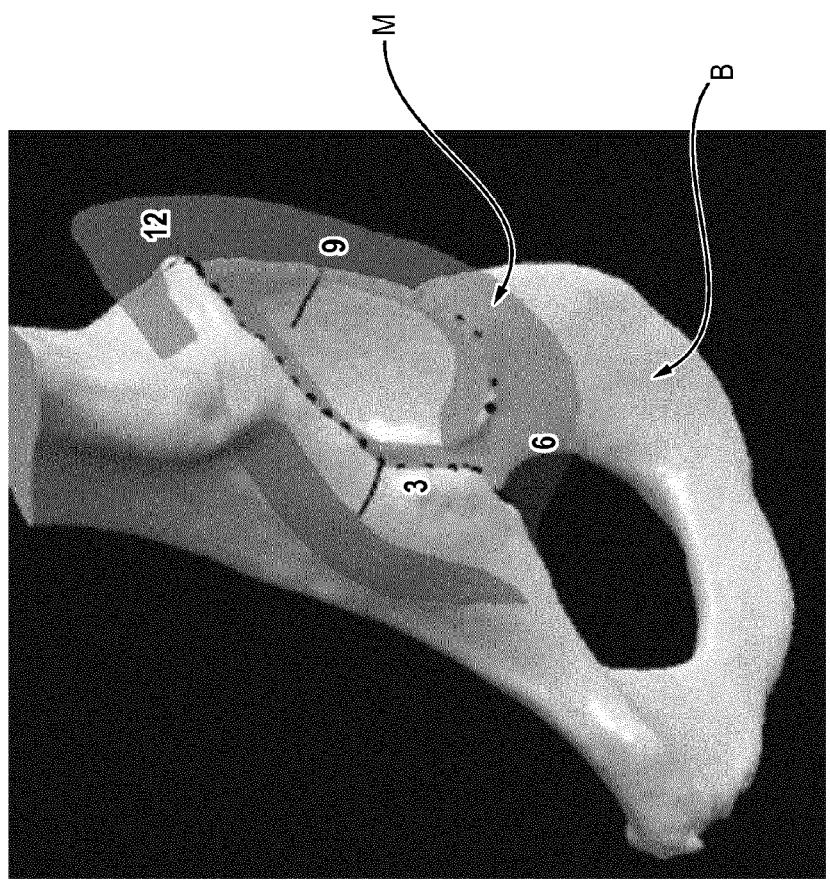

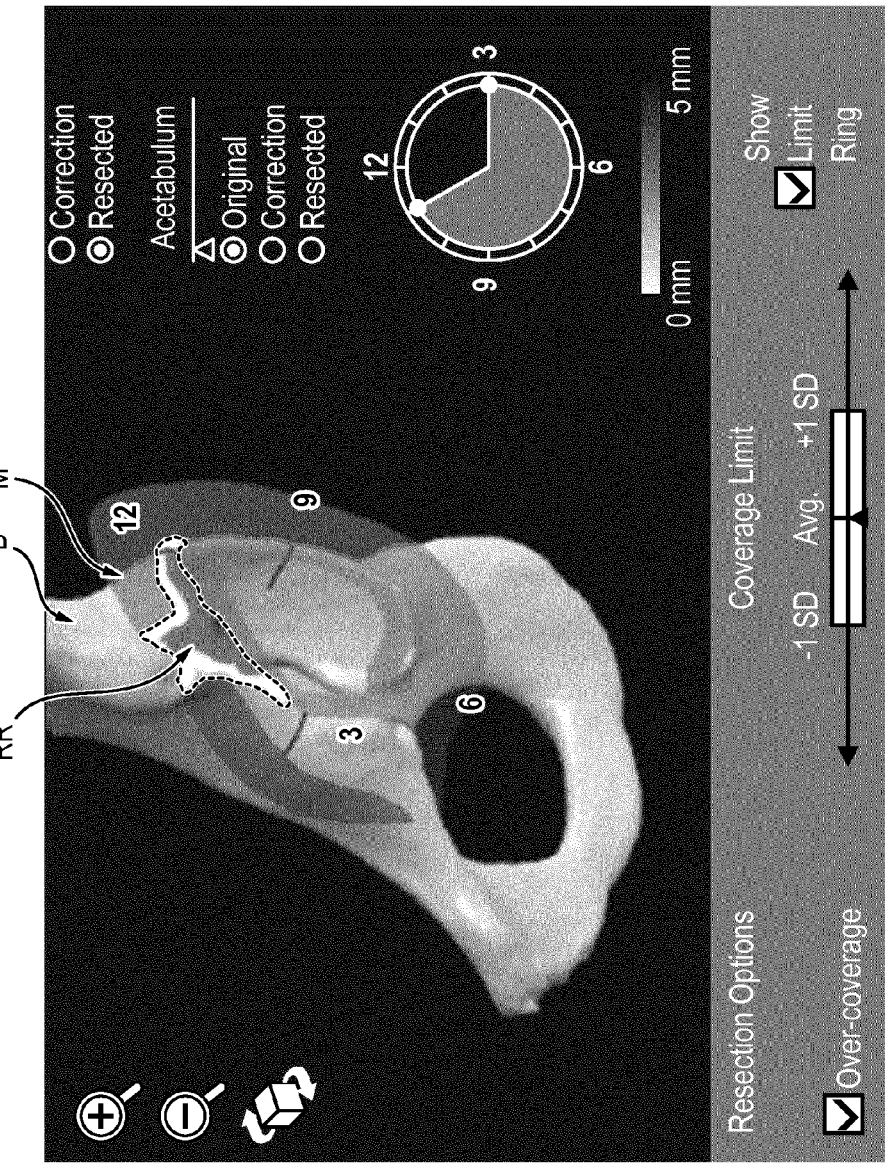

METHOD FOR CREATING A SURGICAL RESECTION PLAN FOR TREATING A PATHOLOGICAL DEFORMITY OF A BONE

CROSS-REFERENCE TO RELATED APPLICATIONS

This application is a US National Phase application under 35 USC §371 from PCT/EP2014/066014 (WO 2015/011256), International filing date Jul. 25, 2014, which claims priority to foreign application no. EP 13306077.2, filed Jul. 25, 2013. The disclosure of prior applications is herein incorporated by reference in their entirety.

FIELD OF THE INVENTION

The invention relates to a method for creating a surgical resection plan for treating a pathological deformity of a bone having a rim bounding a substantially hemispherical cavity of a bone.

BACKGROUND OF THE INVENTION

The acetabulum is a part of the pelvis that comprises a substantially hemispherical cavity for receiving the femoral head which has a corresponding substantially spherical shape to form the hip joint.

The substantially hemispherical cavity of the acetabulum is bounded by the acetabular rim, which has a 3D contour.

In some cases, the acetabulum may suffer from a deformity that generated either over-coverage or under-coverage of the acetabulum with respect to the substantially hemispherical cavity.

An over-covered acetabulum causes a pincer lesion femoro-acetabular impingement (FAI) that limits the range of motion of the hip joint and leads to a conflict between the acetabulum and the femur.

To the contrary, an under-covered acetabulum causes hip dysplasia that leads to a lack of stability of the hip joint.

Surgical intervention for treatment of acetabular under-coverage (i.e. hip dysplasia) and over-coverage (i.e. pincer lesion in femoro-acetabular impingement (FAI)) has become an increasingly common procedure in the field of orthopaedic surgery.

In particular, a pincer lesion can be treated by resecting a part of the acetabulum in the region of the rim where over-coverage has been detected using either an arthroscopic or open surgical approach.

Hip dysplasia is often treated surgically with a peri-acetabular osteotomy (PAO) or total hip arthroplasty.

However, the current diagnostic methods for assessing acetabular coverage are primarily based on conventional 2D X-ray projection imaging or single CT/MRI slices and fail to appreciate the 3D nature of the acetabular deformity.

The most common X-ray measure of acetabular coverage is the lateral center-edge angle (CE angle), which only measures acetabular coverage at one location along the rim R, i.e. the most lateral point, as shown on FIG. 1A.

The cross-over sign is also used to identify cases of anterior over-coverage.

FIG. 1B illustrates an example of the measurement of the cross-over sign CO on a 2D X-ray image of the acetabulum.

However, the cross-over sign only provides a qualitative description of the anterior rim relative to the posterior rim.

In addition, various other measures, such as acetabular version, have been used in view of the assessment of the acetabular morphology, but they fail to provide an objective method of determining 3D pathologic coverage around the entire extent of the acetabulum.

Another method that has been used to assess acetabular coverage is based on 3D renderings generated from 3D medical images such as CT or MRI medical images.

Such a method is based on segmentation of the images to create 3D surface models of the acetabular morphology.

The surgeon can then perform a qualitative visual assessment of the acetabular coverage in order to determine whether surgery is appropriate and, if so, approximately define how much and where to resect the acetabular rim in the case of pincer FAI.

However, this method of visual acetabular coverage assessment is highly subjective, dependent on the surgeon's experience and interpretation of the 3D images.

Hence, there is currently no way for surgeons to assess the 3D acetabular morphology and to create a patient-specific pre-surgical plan that is capable of precisely identifying both the extent and the amount of bone to correct along the acetabular rim.

Thus, many patients receive an unnecessary, insufficient or over-aggressive surgical treatment of their acetabular pathology as a direct result of inadequate pre-operative 3D acetabular morphology assessment techniques.

Similar problems may arise in bones which have, like the acetabulum, a substantially hemispherical cavity bounded by a rim, e.g. the glenoid of the shoulder.

A goal of the invention is thus to overcome the above-mentioned problems and to provide a method for creating a surgical resection plan for treating a pathologic deformity of a bone having a rim bounding a substantially spherical cavity.

BRIEF DESCRIPTION OF THE INVENTION

The invention provides a method for creating a surgical resection plan for treating a pathological deformity of a bone having a rim bounding a substantially hemispherical cavity of the bone, comprising:
  receiving a set of 3D medical images of said bone,
  defining from said 3D medical images patient anatomical landmark data comprising a center of said substantially hemispherical cavity in a patient referential, a rim axis extending from said center and generally perpendicular to the opening plane of said substantially hemispherical cavity, a circumferential coordinate system assigned to said rim and a plurality of points located along the rim,
  determining from said patient anatomical landmark data a 3D patient coverage curve comprising, in the circumferential coordinate system assigned to the rim, a plurality of points representing a coverage parameter of the bone with respect to the substantially hemispherical cavity at a plurality of points along the rim, wherein, for each of said plurality of rim points, said coverage parameter is computed from the coverage angle between (i) the rim axis and (ii) a radius connecting the center of the substantially hemispherical cavity and the respective rim point,
  receiving reference data corresponding to a reference rim morphology, said data comprising a 3D reference coverage curve,
  comparing the 3D patient coverage curve and the 3D reference coverage curve.
  creating:
    a 3D surface model of at least a part of the bone including the rim from said set of 3D images, and a 3D reference rim morphology model from the 3D reference coverage curve, computing and displaying a virtual resection of the bone onto the 3D surface model to simulate removal of over-covered bone portions.

Said 3D reference coverage curve is advantageously determined from a cohort of subjects without said pathology by carrying out the following steps:

for each subject of the cohort:
  receiving a set of 3D medical images of said bone and defining from said 3D medical images patient anatomical landmark data comprising a center of said substantially hemispherical cavity in a patient referential, a rim axis, a circumferential coordinate system assigned to said rim and a plurality of points located along the rim,
  measuring a coverage parameter of the bone with respect to the substantially hemispherical cavity at a plurality of points along the rim,
averaging the measured coverage parameter for each of said plurality of points along the rim for the cohort,
constructing the 3D reference coverage curve in the circumferential rim coordinate system based on the average coverage parameter at said plurality of points along the rim.

According to an embodiment, the method further comprises calculating the coverage parameter standard deviation for each of said plurality of points along the rim for the cohort and constructing the 3D reference coverage curve in the circumferential rim coordinate system based on the average coverage parameter and the standard deviation at said plurality of points along the rim.

According to an embodiment, the 3D reference coverage curve is selected from a database of 3D reference coverage curves, each 3D reference coverage curve being assigned to a determined population of subjects.

The method may further comprise displaying the 3D surface model and the 3D reference rim morphology model fitted to said 3D surface model. In addition, the method may further comprise interactively adjusting the position and/or orientation of the 3D reference rim morphology model with respect to the 3D surface model.

According to an embodiment, the method comprises displaying the regions of the 3D surface model that are over-covered or under-covered with respect to the 3D reference rim morphology model.

Advantageously, the method may further comprise interactively adjusting said virtual resection by operating a cursor of a graphical interface so as to adjust the reference coverage within a determined range of deviation.

The computation of the virtual resection may advantageously comprise creating a smooth transition between resected and non-resected surfaces.

According to an embodiment, the method comprises displaying said virtual resection using a color scale wherein different depths of resection are represented by different colors.

Preferably, the method comprises interactively adjusting the position and/or orientation of the 3D reference rim morphology model with respect to the 3D surface model.

The set of 3D images may comprise CT images, MR images and/or ultrasound images.

The circumferential coordinate system assigned to the rim is advantageously a clock-face referential or angular polar coordinate system.

According to an embodiment, the rim axis is the medial-lateral anatomic axis of the bone comprising the substantially hemispherical cavity.

Alternatively, the rim axis is normal to the opening plane of the substantially hemispherical cavity.

According to a preferred embodiment, the bone is an acetabulum and the pathology is pincer femoro-acetabular impingement.

The coverage parameter is then preferably determined from a coverage angle between the rim axis and a radius joining the center of the hemispherical cavity and a rim point, measured in an image slice comprising the rim axis.

According to an embodiment, the coverage parameter is expressed as a percentage by dividing the coverage angle by 180°.

The center of the hemispherical cavity may be the center of the femoral head or the acetabulum center; the rim axis may be the medial-lateral axis of the pelvis or the axis normal to the opening plane of the acetabulum.

According to a preferred embodiment, the rim axis is defined as the axis joining the centers of the left and right femoral heads of the patient.

Another object of the invention is a computer program product comprising computer-readable instructions which, when loaded and executed on a suitable system, perform the steps of a surgical resection plan creation method as described above.

Said computer program product may be on any physical support such as a memory of a CD-ROM for example.

BRIEF DESCRIPTION OF THE DRAWINGS

Other features and advantages of the invention will be apparent from the detailed description that follows, based on appended drawings, wherein:

FIG. 5 shows the visualization of a 3D reference rim morphology model fitted to the 3D surface model of the acetabulum of the patient;

FIGS. 6A and 6B illustrate a graphical user interface allowing the visualization of a simulated resection for different adjustment options of the 3D average coverage curve (respectively based on the average coverage and on the average coverage minus 1 SD); the resection depth is illustrated by a color scale.

DETAILED DESCRIPTION OF EMBODIMENTS OF THE INVENTION

Figure 1B:
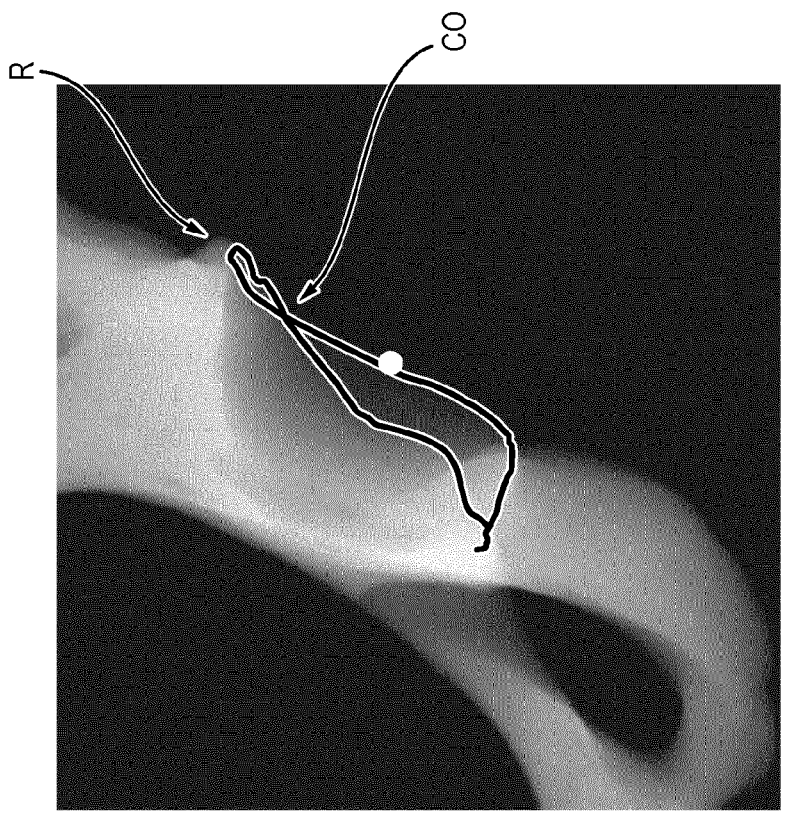
FIG. 1B shows the assessment of the cross-over sign on a 2D X-ray image of the acetabulum in a conventional acetabular morphology assessment procedure.
Figure 1A:
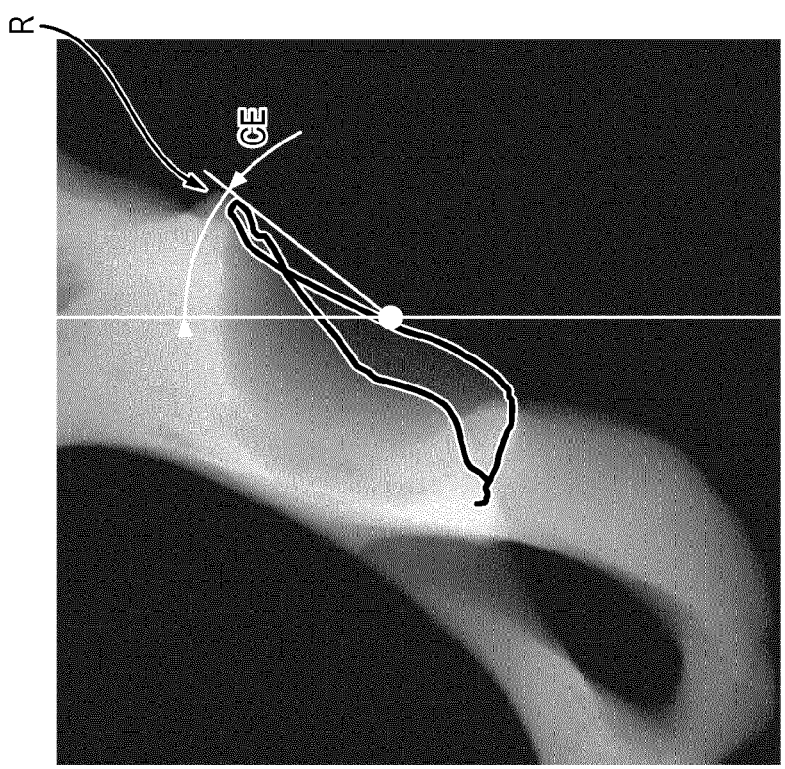
FIG. 1A shows the measurement of the lateral center-edge angle on a 2D X-ray image of the acetabulum in a conventional acetabular morphology assessment procedure.

The detailed description that follows is focused on the hip joint, and more specifically to the acetabulum, in view of assessing and developing a pre-surgical plan for acetabular over-coverage or under-coverage, which may cause pincer femoro-acetabular impingement or hip dysplasia, respectively.

However, the invention may be applied for 3D assessment of similar pathologies in other joints comprising a bone having a rim bounding a substantially hemispherical cavity.

For example, the coverage of the glenoid of the shoulder can be determined and visualized in the same way as described below for the acetabulum.

Hence, although the description that follows refers to the acetabulum and the acetabular rim, the scope of the invention is not limited to the hip joint.

The method is carried out in a system comprising a computer and a screen for displaying the results of the 3D assessment of a pathological deformity of the acetabulum.

In some embodiments, the volume to be resected in case of an over-covered acetabulum can be visualized.

A software can be implemented on the computer to carry out the method.

The system also comprises a graphical user interface (GUI) that provides an interaction between a user and the software, in particular to allow the user to adjust the parameters of the comparison between the patient morphology and the reference morphology and/or to control the resection options.

The graphical user interface may be displayed on the above-mentioned screen.

Determination of Acetabular Coverage Parameter

The definition of the morphologic parameters of the acetabulum is based on the treatment of 3D medical images of the acetabulum of a subject.

Said subject may be either a patient suffering from acetabular deformity that is intended to be assessed or an asymptomatic subject, e.g. in view of defining a reference morphology of the rim.

Said 3D medical images may be acquired by CT, MRI and/or ultrasound.

For example, the 3D images may be a bilateral pelvis 3D CT scan.

Anatomical landmarks of the hip joint can be computed automatically and/or with manual methods, and 3D measurements characterizing the coverage of the acetabulum can be carried out.

The identified anatomical landmarks of the hip joint are used to define axes and an origin, forming an anatomic coordinate system. The acetabular rim landmarks are then identified and the coverage parameter of the acetabulum can be calculated at a plurality of locations along the rim, measured as angles or percentages relative to the anatomic coordinate system.

According to an advantageous embodiment, a best-fit sphere is calculated to determine the femoral head anatomical landmarks on each side.

The center of the best-fit sphere may then be considered to be the center of the femoral head.

There are several methods for computing the best-fit sphere to the femoral head. One example of a method for determining the best-fit sphere is to apply a robust least-square fitting of a sphere to a set of 3D points representing the cortical surface of the femoral head.

Optionally, the best-fit sphere to the femoral head can be determined by manual fitting of circles to the femoral head in at least two orthogonal 2D reformatted medical images.

Next, a rim axis is determined, which is an axis generally perpendicular to the opening plane of the substantially hemispherical cavity. By "generally perpendicular" is meant in the present text an axis normal to the opening plane or the medial-lateral anatomic axis of the bone comprising the cavity, said medial-lateral axis extending substantially in the same direction as the normal to the opening plane.

For example, in the case of hip joint, the medial-lateral axis of the pelvis extends in the medial-lateral anatomic direction of the pelvis. Said medial-lateral axis of the pelvis is generally perpendicular to the opening plane of the acetabulum.

For the application at the shoulder, the medial-lateral axis would extend in the medial-lateral anatomic direction of the scapula. Said medial-lateral axis of the scapula is generally perpendicular to the opening plane of the glenoid.

There are several methods for determining a medial-lateral axis of the pelvis. In one example, a medial-lateral axis of the pelvis is defined as the line joining the femoral head centers.

Optionally, the medial-lateral axis of the pelvis can be defined by the line joining the acetabular centers, where the acetabular centers are defined by fitting a sphere to the articulating surface of the acetabulum or by calculating the centroid of the set of 3D points representing the acetabular rim.

An additional option for determining the rim axis is to use the vector normal to a plane fit to the set of 3D points representing the acetabular rim, also called the opening plane of the acetabulum.

Defining the medial-lateral rim axis using the centers of the left and right femoral heads or acetabular centers is particularly advantageous because it provides a basis for creating a 3D acetabular rim coverage parameter that takes into account variations in coverage due to both overall acetabular orientation (such as acetabular retroversion) and regional variations in the shape of the acetabular rim. Using a rim axis only fit to the opening plane of the acetabulum to create a 3D acetabular coverage parameter only takes into account the regional variations in the shape of the acetabular rim, but not variations in the overall acetabular orientation (such as acetabular retroversion).

Then, each side of the pelvis can be processed separately for analysis of the respective acetabulum.

To that end, the acetabulum volume can be separated from the femur volume in the 3D medical images using standard image processing methods.

For each acetabular side, the acetabulum rim can be detected automatically and/or with manual methods.

An example method for detecting the acetabular rim is to identify the rim points in reformatted radial 2D medical images, with the radial images formed by rotating about the medial-lateral axis of the pelvis. In each image, the rim point is defined as the first point of contact of a radius rotating from the lateral to medial direction about the femoral head center or other point approximating the acetabular center.

For example, said detection generates a series of points distributed radially every 7.5° (corresponding to ¼ h on a clock-face) along the rim.

Due to the rim shape, a preferred coordinate system that can be assigned to the rim is a circumferential coordinate system.

According to an embodiment, a 2D clock-face circumferential coordinate system can be assigned to the rim such that the 6 o'clock position corresponds to the inferior acetabular notch.

According to another embodiment, a 2D polar circumferential coordinate system can be assigned to the rim such that the 0 degree position corresponds to the inferior acetabular notch.

Then, a 3D acetabular coordinate system can be constructed.

The origin of this 3D coordinate system is defined as the center of the substantially hemispherical joint cavity, such as the femoral head center point or acetabular center point. The orthogonal axes of the 3D coordinate system are created using the medial-lateral pelvic axis (which forms here the rim axis) and the 2D circumferential coordinate system assigned to the rim.

For example, a vector cross product of medial-lateral pelvic axis with a temporary axis created from the origin to a specified point on the acetabulum, such as the 6 o'clock position at the inferior acetabular notch, can be used to create the three orthogonal axes of the 3D acetabular coordinate system.

From these anatomical elements, the acetabular coverage parameter can be defined.

Figure 2B:
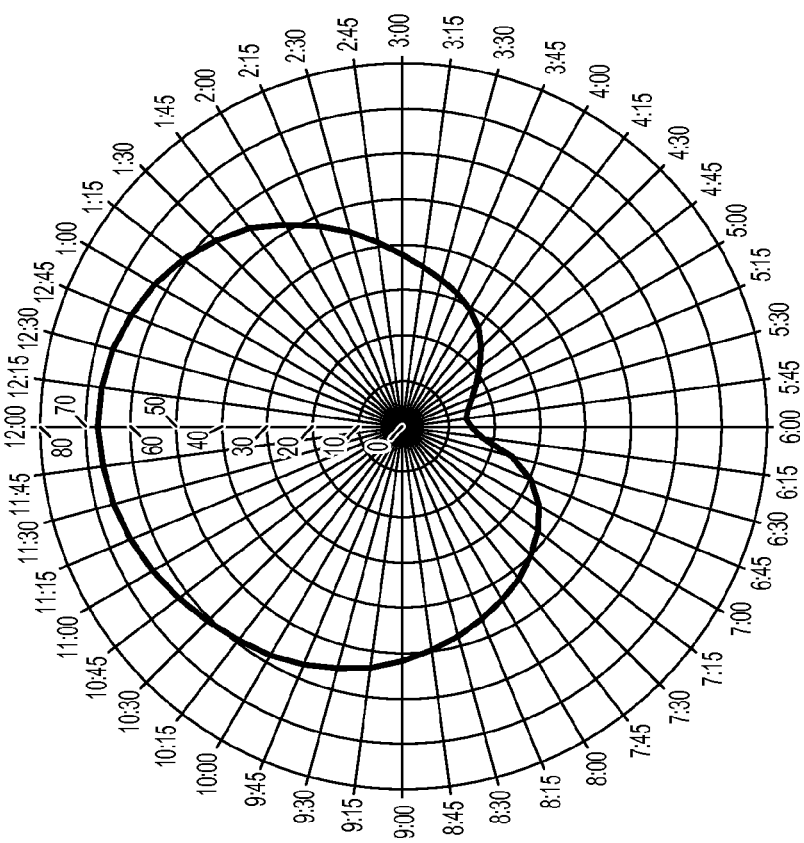
FIG. 2B illustrates a 3D percentage coverage curve in the acetabular clock-face.
Figure 2A:
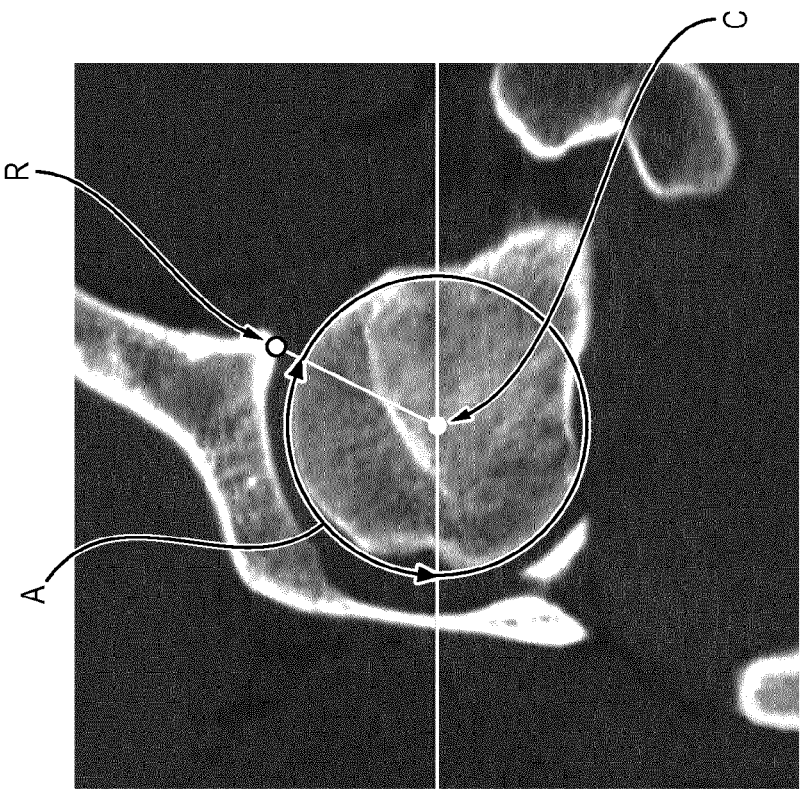
FIG. 2A illustrates the calculation of the coverage parameter by measuring the angle between the medial-lateral axis of the pelvis and a radius joining the femoral head center and a rim point in a radial CT slice.

As shown in FIG. 2A, the coverage angle A between the pelvic medial-lateral axis ML and the radius connecting the femoral head center C and an point of the acetabular rim R is measured in radial CT slices around the pelvic medial-lateral axis.

This angle can be converted to a percentage coverage by dividing it by 180°.

The percentage coverage can be measured at different positions around the rim, in the appropriate reformatted radial image slice.

Then, these measures can be used to define a 3D coverage curve, as shown in FIG. 2B.

This 3D coverage curve is formed of points representing, in the circumferential rim coordinate system of the subject, a coverage parameter of the acetabulum with respect to the substantially hemispherical cavity at a plurality of points along the rim.

According to a preferred embodiment, the coverage parameter is the coverage percentage as defined above.

Alternatively, the coverage parameter can be the angle itself.

In an alternative embodiment, instead of defining the coverage parameter based on a radius from the femoral head center, the radius could extend from the acetabular center.

Reference Data

According to an embodiment, reference data corresponding to a reference rim morphology have been obtained by analyzing the acetabulum of a cohort of subjects, by determining, for each subject, the coverage parameter at each point around the circumferential rim coordinate system in accordance with the method described above, and finally by calculating the average and standard deviation of the coverage parameter at each location in the circumferential rim coordinate system for the cohort.

Since the reference data are intended to provide a normative acetabular morphology, a cohort of asymptomatic subjects is selected.

It is possible to refine the normative data by selecting different groups of subjects rather than using a population of normal hips and to define a reference rim morphology for each of these groups.

For example, each group may be constituted based on given criteria such as age, gender, ethnicity or height/weight.

In such case, the reference data will be determined specifically for each group of subjects. This feature is advantageous because it allows the creation of a pre-surgical plan specifically designed for the patient being assessed. The person planning the surgical procedure can pick the most appropriate reference curve based on the individual's characteristics, rather than using the same reference curve for all patients.

By "average" is meant here the result obtained by adding the coverage parameter of each subject of the cohort and dividing this sum by the number of subjects of the cohort, for each point around the acetabular clock-face.

The standard deviation (SD), which is the dispersion from the average, can also be computed to characterize the distribution of coverage in the cohort at each clock position.

The determination of the standard deviation of the coverage is particularly advantageous because it allows for the comparison of the patient's coverage curve relative to a reference curve that is allowed to vary within certain normal bounds based on the measured reference standard deviation at each clock position, which takes into account the natural inter-subject coverage variability. The person planning the surgical procedure can then assess the patient's coverage relative to the normal range of coverage at each clock position, rather than correcting every patient to an average population value which may not be appropriate for all patients.

The average coverage parameter is defined as the reference coverage parameter for a given point along the rim.

The 3D reference coverage curve comprises, in the reference coordinate system, a plurality of points representing a reference coverage parameter of the bone with respect to the substantially hemispherical cavity at a plurality of points along the rim.

Said reference coordinate system, in which the 3D reference coverage curve is characterized, is preferably defined using the same method as described above for the 3D acetabular coordinate system.

Expression of the 3D reference coverage curve in a consistently-defined reference coordinate system allows direct comparison of 3D coverage curves between different subjects and between 3D reference coverage curves.

This 3D reference coverage curve will then be stored on a suitable medium so as to be able to be loaded upon request by the user and to be used as a reference for the assessment of the morphology of an acetabular deformity of a patient.

Figure 3:
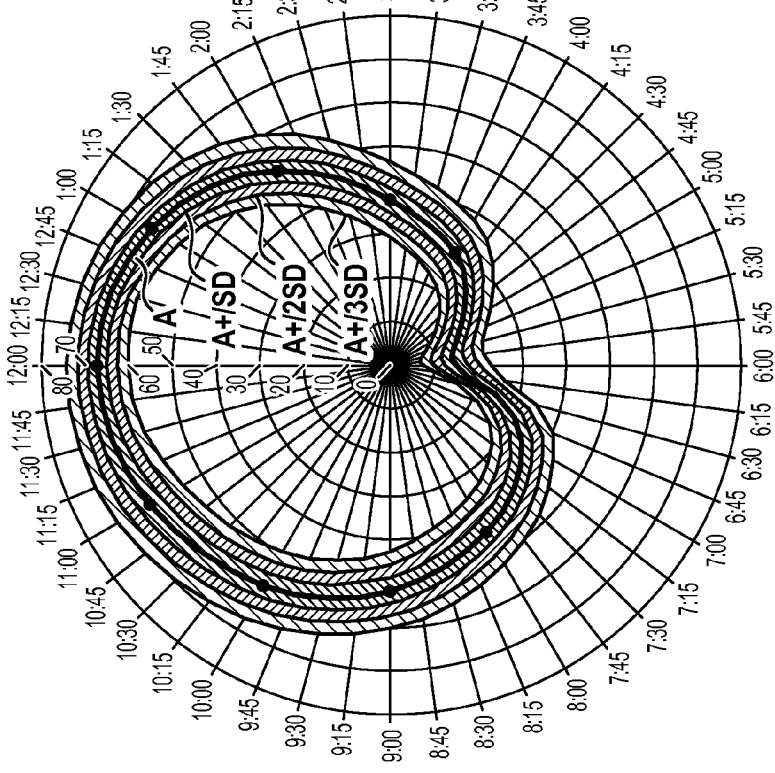
FIG. 3 illustrates a 3D average coverage curve with three intervals of standard deviation, determined from a cohort of asymptomatic subjects.

FIG. 3 shows an example of a 3D reference coverage curve obtained from a cohort of subjects in a clock-face circumferential system.

In this example, the average curve A is shown, along with regions corresponding respectively to the average±the standard deviation (interval referred to as A±SD), the average±twice the standard deviation (interval referred to as A±2 SD) and the average±3 times the standard deviation (interval referred to as A±3 SD).

As mentioned above, it would be possible to define a more specific reference curve for a given population, by carrying out the determination of the average acetabular coverage for this specific population.

In some embodiments, once the 3D reference acetabular coverage curve is defined, a radius can be specified to create a 3D reference rim morphology model.

Said radius may be determined automatically or may be adjusted by the user via the graphical user interface.

According to an embodiment, the origin from which said radius extends can be the femoral head center that has been determined previously.

According to an alternative embodiment, the acetabular center can be determined and serve as the origin for the 3D reference rim morphology.

As will be explained below, the 3D reference rim morphology model can then be fitted to a 3D surface model of the acetabulum of a patient to visualize the extent of over or under-coverage.

Determination of Patient-Specific Regions of Acetabular Over or Under-Coverage

A patient-specific 3D coverage curve is determined by the method described above based on 3D medical images of the acetabulum of a patient.

Said 3D medical images may have been acquired previously by CT, MRI and/or ultrasound and stored on a suitable medium so as to be able to be loaded upon request by the user.

A next step is a comparison of the 3D patient coverage curve and the 3D reference coverage curve and the determination of a virtual resection plan simulating removal of over-covered bone portions.

As will be described below, said comparison can be carried out in different ways.

Provided that the 3D reference coverage curve and 3D patient coverage curve are generated using the same method with the same coordinate system definition, the 3D reference coverage curve can thus be compared to the 3D coverage curve of the patient, in order to assess the morphology of the patient's acetabulum.

According to an embodiment, the comparison is carried out on the 3D coverage curves directly.

For example, the 3D reference coverage curve and the 3D patient coverage curve can be superimposed.

It is then possible to visualize and to calculate the difference between the patient and reference coverage parameters at each position in the circumferential rim coordinate system.

If the 3D patient coverage is locally greater than the 3D reference coverage, it can be considered that the acetabulum is locally over-covered.

To the contrary, if the 3D patient coverage is locally smaller than the 3D reference coverage, it can be considered that the acetabulum is locally under-covered.

In addition, since each of the 3D reference coverage curve and the 3D patient coverage curve are associated to local coverage values, this comparison provides a quantitative assessment of the over or under-coverage of the patient's acetabulum.

Such a quantitative assessment allows determining, in the case of pincer FAI, the extent to which the acetabulum should be resected to obtain a reference coverage.

Figure 4:
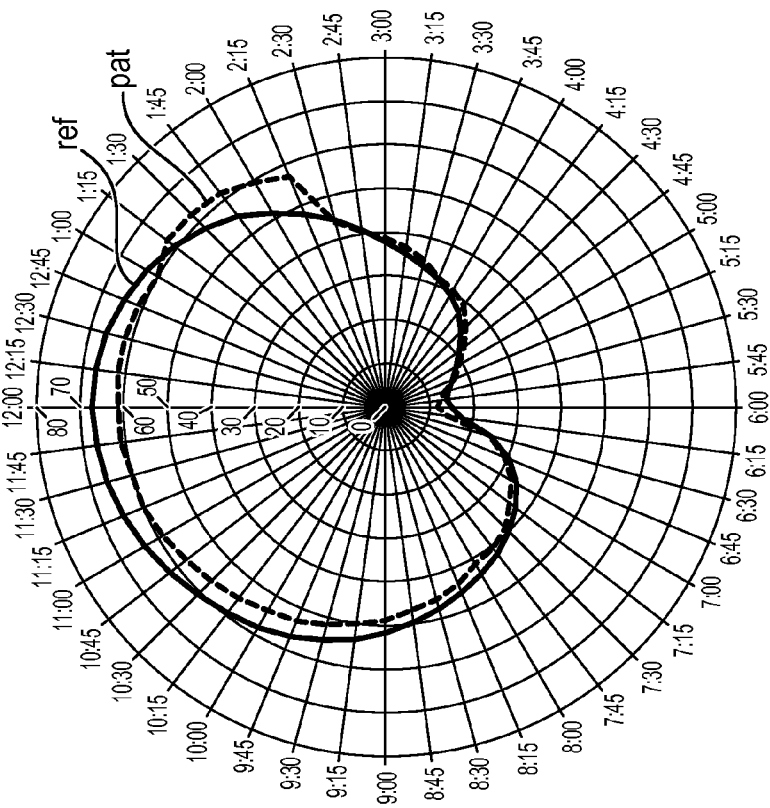
FIG. 4 shows the superimposition of a 3D reference coverage curve and a 3D patient coverage curve exhibiting local over-coverage.

FIG. 4 shows an example of a comparison of a 3D reference curve noted ref (only the average has been displayed here) and a 3D patient curve noted pat in a clock-face coordinate system.

It can be seen from the superimposition of both curves that the patient suffers from an over-coverage between the 1:15 and 2:30 o'clock positions.

According to an embodiment, a visual comparison is carried out on a 3D surface model B of the acetabulum and on a 3D reference rim morphology model M, as shown in FIG. 5.

Only the 3, 6, 9 and 12 o'clock positions of the clock-face circumferential coordinate system are represented on this figure.

To that end, a 3D surface model of the acetabulum of the patient can be created from the 3D images by known techniques such as segmentation.

The 3D reference rim morphology model can be created from the 3D reference coverage curve by specifying a radius extending from the reference center of the substantially hemispherical cavity to the rim.

The 3D reference rim morphology model is thus analogous to a surface that can be fitted to the 3D surface model of the acetabulum of the patient.

Said fitting comprises aligning the 3D acetabular coordinate systems of the 3D surface model of the acetabulum and of the 3D reference rim morphology model.

In some embodiments, the user is able to adjust the position of the 3D reference rim morphology model in an interval between the average coverage and ±1 SD for example.

To this end, the graphical user interface comprises one cursor (see FIGS. 6A and 6B) that can be activated by the user between a position corresponding to the average coverage minus 1 SD and the average coverage plus 1 SD.

The interactive adjustment of the 3D reference rim model through a graphical user interface is useful because it allows the user to easily and quickly visualize different rim resection options. This feature provides the user with a tool to compare different rim resection options in order to better understand the degree of acetabular pathology and then to select the most appropriate rim resection option for the individual patient based on their clinical judgment. This feature is preferred to the alternative option that only performs the acetabular rim coverage assessment using a single, fixed 3D reference rim model.

Of course, any other range could be selected for the interactive adjustment controls.

In the case of FIG. 6A, the cursor is set on the average coverage.

Figure 6B:
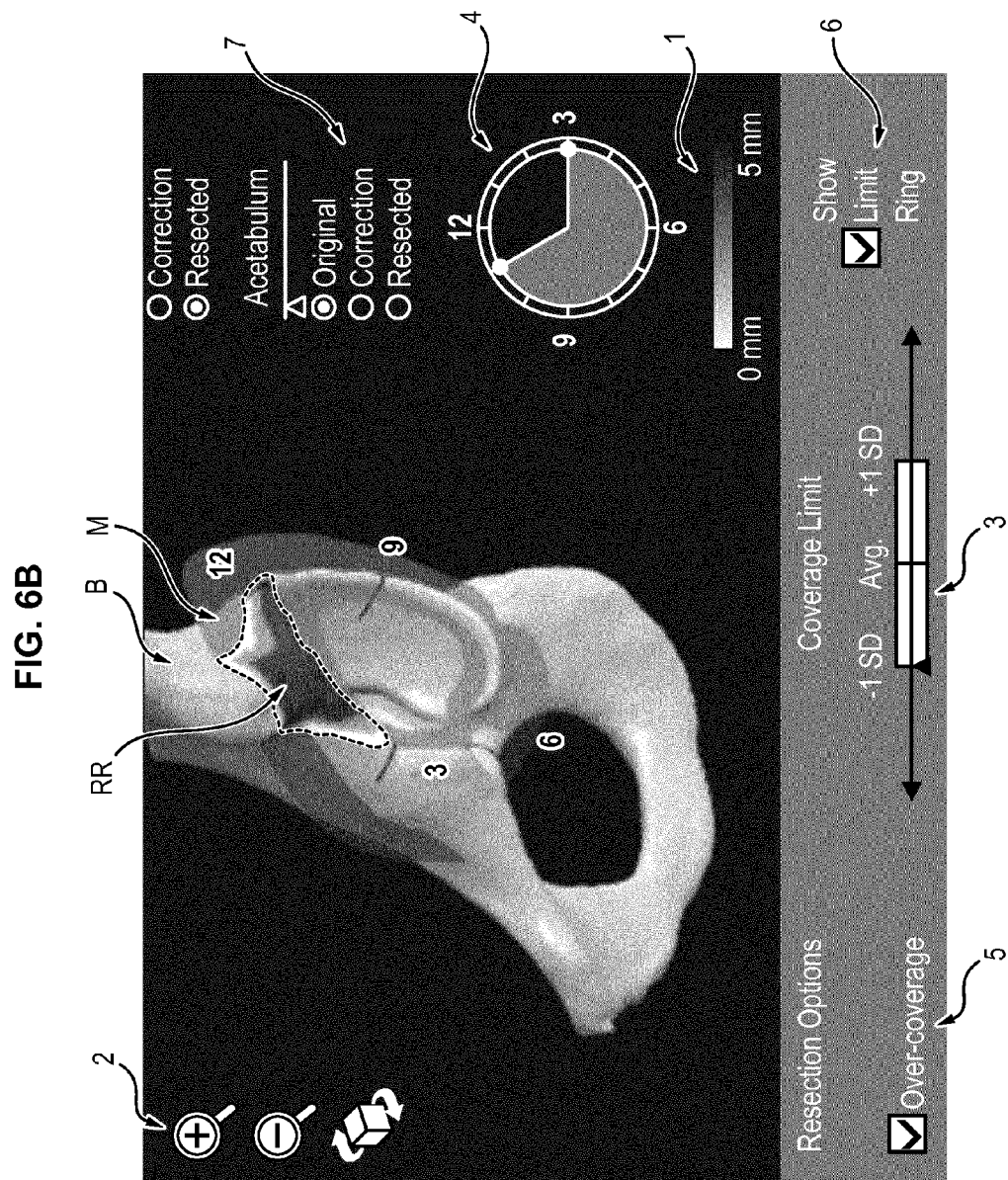

In the case of FIG. 6B, the cursor is set on the average coverage minus 1 SD.

According to an embodiment, a resection to be applied to the patient can be virtually determined and visualized using a color scale wherein different depths of resection are represented by different colors.

The visualization of the actual virtual bony resection or color scale representation of the planned resection on the 3D acetabular model is advantageous because it presents the resection plan in a 3D view that is consistent with the way that surgeons commonly view 3D CT data as well as the 3D view that they visualize during the surgical procedure. This is advantageous over the display of the 2D patient acetabular coverage curve relative to the 2D reference coverage curve, which may be difficult to visualize and translate to the actual 3D bony anatomy of the patient during the surgical procedure.

Advantageously, the calculation and display of the 3D reference rim morphology model, and the subsequent virtual bone resection, can be performed automatically, based on automated detection of the relevant anatomic landmarks.

It is also possible to combine the 3D reference rim morphology model with other methods for determining the resection, e.g. methods based on simulated dynamic impingement volume or local manual manipulation of the resection shape on a radial image.

Preferably, the calculated resection region is smoothed at its endpoints along the clock-face so as to create a smooth transition with the non-resected acetabular rim. For example, the smooth transition could be created using a linear interpolation between the resected and non-resected acetabular rim points.

According to an embodiment, the circumferential extent of the resection can be limited to only clinically relevant areas and/or adjustable by the user.

For example, said areas are comprised between the following clock positions in the clock-face circumferential system: 11 o'clock to 3 o'clock. This region is where pincer lesions are often located and represent regions of the acetabular rim accessible using an arthroscopic surgical approach.

According to an embodiment, the 3D reference rim morphology model is not displayed.

For instance, only the resulting identification of the over or under-covered regions of the acetabulum is displayed.

Indeed, the main information necessary to determine the over or under-covered regions results from the comparison of the 3D patient coverage curve and the 3D reference coverage curve, since these curves provide a quantitative assessment of the acetabular morphology.

The 3D reference rim morphology model and 3D patient bone model are rather used to allow 3D visualization of the patient's morphology and/or of the simulated resection.

Hence, the invention provides an easy-to-use and precise method of determining and displaying 3D acetabular over or under-coverage from 3D images.

In particular, this method is automated and provides an objective and comprehensive assessment of the 3D morphology of the acetabulum around the entire rim circumference.

In addition, the determined acetabular regions of over or under-coverage are completely 3D and not limited to specific imaging planes.

It can be noted that other methods have also been described to assess the 3D acetabular rim coverage around the cock-face relative to an acetabular rim axis (Cobb 2010). However, this study presented a method that required a manual process and only compared pathologic hips with a small group of control hips. Further, since the acetabular rim axis was defined as the axis normal to the acetabular opening plane, it was not possible to assess the interaction between acetabular version and acetabular rim coverage at the different clock-face positions (i.e. if the patient had global acetabular retroversion and a normal acetabular rim shape, this method would not detect that the patient had excessive anterior acetabular rim coverage). Finally, this study did not provide any instruction on how this method could be applied to generate and visualize a virtual pre-surgical resection plan on the 3D acetabular bone model or any means for interactively adjusting the reference rim coverage curve to develop a patient-specific resection plan (rather than using the same reference rim coverage curve for the assessment of all patients).

Operation of the Software and of the Graphical User Interface

In view of assessing acetabular deformity for a patient, the user loads a set of 3D medical images of the pelvis of the patient from a storage medium.

The software automatically detects relevant anatomic landmarks in said 3D medical images and determines the medial-lateral axis of the pelvis.

Then, the acetabular rim points are automatically detected and a 2D circumferential (e.g. clock-face or angular polar) coordinate system is assigned to the rim as described above.

The software computes, in each radial slice around the circumference of the acetabulum, the angle between the pelvic medial-lateral axis and the radius connecting the femoral head center and acetabular rim point.

This angle is converted to a percentage by dividing by 180°.

The 3D patient coverage curve is computed in the patient coordinate system from the coverage percentage at each position.

This 3D curve may be displayed on the screen.

The software further loads a 3D reference coverage curve from a storage medium.

There may exist several reference coverage curves, each assigned to a determined population, and the user may select, using the graphical user interface, a coverage curve for a population to whom the patient belongs, e.g. depending on age, gender, ethnicity or height/weight of the patient.

In such case, the graphical user interface can allow the user to select the desired model for the patient among available models.

The software then computes, for each position in the circumferential rim coordinate system, the difference between the 3D patient coverage and the 3D reference coverage.

The standard deviation can be taken into account to determine the regions of the acetabulum where a resection would be appropriate.

For example, it can be considered that if the patient coverage is within the standard deviation interval, there is no need to carry out a resection.

The software may also compute a 3D acetabulum surface model from the set of 3D images.

The software may also compute the 3D reference rim morphology model by specifying a radius extending from the femoral head center.

According to an embodiment, the superimposition of the 3D acetabulum surface model and the 3D reference rim morphology can be displayed on the screen, so as to supply to the user a visual representation that may help him to determine regions of pathologic over-coverage to resect in the case of pincer FAI.

The default position and average rim morphology is automatically displayed by the software.

However, it can be interactively adjusted by the user via the graphical user interface based on a clinical judgment.

In addition, the display of the 3D reference rim morphology model can be turned on or off by the user through the graphical user interface.

According to an embodiment, the user can use the graphical user interface of the software to interactively determine the region and amount of the acetabulum to resect in case of over-coverage.

FIG. 5B illustrates a non-limitative embodiment of the graphical user interface.

In this example, the 3D surface model B of the patient's acetabulum and the 3D reference rim morphology model R are displayed, together with the simulated resection RR.

The simulated resection region is visually depicted using a color scale 1 with different colors depending on the depth of resection.

The graphical user interface also comprises buttons 2 that allow zooming in and out and modifying the orientation of the 3D models.

The graphical user interface further comprises a cursor 3 that allows the user to adjust the 3D reference rim morphology model between the average coverage and ±1 SD.

The graphical user interface also comprises an interactive tool 4 that allows the user to control the circumferential extent of the resection around the clock-face.

In the illustrated example, said circumferential extent is comprised between the 11 o'clock and 3 o'clock positions.

The graphical user interface further comprises buttons 5, 6, 7 allowing the user to select the models he wants to visualize.

For example, button 5 allows selecting the visualization of the over-covered regions.

Button 6 allows selecting the visualization of the 3D reference rim morphology model.

Button 7 allows selecting the visualization of the 3D surface model of the original acetabulum, of the corrected acetabulum and/or of the resection regions.

Of course, many other options could be inserted in the graphical user interface without departing from the scope of the present invention.

REFERENCES (Cobb 2010) Justin Cobb et al, "Cams and Pincer Impingement Are Distinct, Not Mixed: The Acetabular Pathomorphology of Femoroacetabular Impingement", Clinical Orthopaedics and Related Research, vol. 468, no. 8, 30 Apr. 2010

The invention claimed is:

1. Method for creating a surgical resection plan for treating a pathological deformity of a bone having a rim bounding a substantially hemispherical cavity of the bone, comprising:
   receiving a set of 3D medical images of said bone,
   defining from said 3D medical images patient anatomical landmark data comprising a center of said substantially hemispherical cavity in a patient referential, a rim axis extending from said center and generally perpendicular to the opening plane of said substantially hemispherical cavity, a circumferential coordinate system assigned to said rim and a plurality of points located along the rim,
   determining from said patient anatomical landmark data a 3D patient coverage curve comprising, in the circumferential coordinate system assigned to the rim, a plurality of points representing a coverage parameter of the bone with respect to the substantially hemispherical cavity at a plurality of points along the rim, wherein, for each of said plurality of rim points, said coverage parameter is computed from the coverage angle between (i) the rim axis and (ii) a radius connecting the center of the substantially hemispherical cavity and the respective rim point,
   receiving reference data corresponding to a reference rim morphology, said data comprising a 3D reference coverage curve,
   creating:
      a 3D surface model of at least a part of the bone including the rim from said set of 3D images, and
      a 3D reference rim morphology model from the 3D reference coverage curve,
   computing and displaying a virtual resection of the bone onto the 3D surface model to
   simulate removal of over-covered bone portions.

2. The method of claim 1, wherein the 3D reference coverage curve is determined from a cohort of subjects without said pathology by carrying out the following steps:
   for each subject of the cohort:
      receiving a set of 3D medical images of said bone and defining from said 3D medical images patient anatomical landmark data comprising a center of said substantially hemispherical cavity in a patient referential, a rim axis, a circumferential coordinate system assigned to said rim and a plurality of points located along the rim,
      measuring a coverage parameter of the bone with respect to the substantially hemispherical cavity at a plurality of points along the rim,
   averaging the measured coverage parameter for each of said plurality of points along the rim for the cohort,
   constructing the 3D reference coverage curve in the circumferential rim coordinate system based on the average coverage parameter at said plurality of points along the rim.

3. The method of claim 2, further comprising calculating the coverage parameter standard deviation for each of said plurality of points along the rim for the cohort and constructing the 3D reference coverage curve in the circumferential rim coordinate system based on the average coverage parameter and the standard deviation at said plurality of points along the rim.

4. The method of claim 1, wherein the 3D reference coverage curve is selected from a database of 3D reference coverage curves, each 3D reference coverage curve being assigned to a determined population of subjects.

5. The method of claim 1, further comprising displaying the 3D surface model and the 3D reference rim morphology model fitted to said 3D surface model.

6. The method of claim 5, comprising interactively adjusting the position and/or orientation of the 3D reference rim morphology model with respect to the 3D surface model.

7. The method of claim 1, further comprising displaying the regions of the 3D surface model that are over-covered or under-covered with respect to the 3D reference rim morphology model.

8. The method of claim 1, comprising interactively adjusting said virtual resection by operating a cursor of a graphical interface so as to adjust the reference coverage within a determined range of deviation.

9. The method of claim 1, wherein the computation of the virtual resection comprises creating a smooth transition between resected and non-resected surfaces.

10. The method of claim 1, comprising displaying said virtual resection using a color scale wherein different depths of resection are represented by different colors.

11. The method of claim 1, wherein the set of 3D images comprises CT images, MR images and/or ultrasound images.

12. The method of claim 1, wherein the circumferential coordinate system assigned to the rim is a clock-face referential or angular polar coordinate system.

13. The method of claim 1, wherein the rim axis is the medial-lateral anatomic axis of the bone comprising the substantially hemispherical cavity.

14. The method of claim 1, wherein the rim axis is normal to the opening plane of the substantially hemispherical cavity.

15. The method of claim 1, wherein the bone is an acetabulum and the pathology is pincer femoro-acetabular impingement.

16. The method of claim 15, wherein the coverage parameter is determined from a coverage angle between a medial-lateral axis of the pelvis and a radius joining the center of the hemispherical cavity and a rim point, measured in an image slice comprising the medial-lateral axis.

17. The method of claim 16, wherein the coverage parameter is expressed as a percentage by dividing the coverage angle by 180°.

18. The method of claim 15, wherein the center of the hemispherical cavity is the center of the femoral head or the acetabulum center.

19. The method of claim 15, wherein the rim axis is defined as the axis joining the centers of the left and right femoral heads of the patient.

* * * * *